(12) United States Patent
Zoppetti et al.

(10) Patent No.: US 8,252,770 B2
(45) Date of Patent: Aug. 28, 2012

(54) COMPOSITIONS COMPRISING GLYCOSAMINOGLYCANS OF LOW VISCOSITY AND USE OF SAID COMPOSITION IN THERAPY OF CHRONIC CYSTITIS

(75) Inventors: Giorgio Zoppetti, Milan (IT); Nadia Puppini, Como (IT); Marco Pizzutti, Malnate (IT)

(73) Assignee: Altergon S.A., Lugano (CH)

( * ) Notice: Subject to any disclaimer, the term of this patent is extended or adjusted under 35 U.S.C. 154(b) by 573 days.

(21) Appl. No.: 12/227,761

(22) PCT Filed: May 25, 2007

(86) PCT No.: PCT/EP2007/055107
§ 371 (c)(1),
(2), (4) Date: Nov. 25, 2008

(87) PCT Pub. No.: WO2007/138014
PCT Pub. Date: Dec. 6, 2007

(65) Prior Publication Data
US 2009/0181924 A1   Jul. 16, 2009

(30) Foreign Application Priority Data
Apr. 30, 2007  (IT) .............................. MI2006A1030

(51) Int. Cl.
*A61K 31/70* (2006.01)
(52) U.S. Cl. ......................................... 514/54
(58) Field of Classification Search ........................ None
See application file for complete search history.

(56) References Cited

U.S. PATENT DOCUMENTS
2004/0082540 A1   4/2004   Ochoa

FOREIGN PATENT DOCUMENTS
| EP | 0 136 782 A2 | 4/1985 |
| WO | WO 03/034993 A2 | 5/2003 |
| WO | WO 2004/034980 A2 | 4/2004 |

OTHER PUBLICATIONS

Hardingham, *Solution properties of hyaluronan*, In: Chemistry and Biology of Hyaluronan, Garg and Hales, eds., pp. 1-19 (2004).
Scott et al., Hyaluronan forms specific stable tertiary structures in aqueous solution: A 13C NMR study, *Proc. Natl. Acad. Sci. USA* 96:4850-4855 (1999).
Scott, Structure and function in extracellular matrices depend on interactions between anionic glycosaminoglycans, *Pathol. Biol.* 49:284-289 (2001).
International Search Report and Written Opinion for International Application No. PCT/EP2007/055107, mailed Nov. 9, 2007 from the International Searching Authority of the European Patent Office.

*Primary Examiner* — Elli Peselev
(74) *Attorney, Agent, or Firm* — Finnegan Henderson Farabow Garrett & Dunner, LLP

(57) ABSTRACT

The present invention concerns an aqueous pharmaceutical composition for bladder instillation, cystitis therapy, or interstitial cystitis therapy, the aqueous composition containing water, hyaluronic acid or a salt thereof and/or chondroitin sulphate or a salt thereof, and a pharmaceutically acceptable bivalent metal ion, wherein the bivalent metal ion is chosen from calcium and magnesium, and wherein the bivalent ion lowers the viscosity of the composition.

10 Claims, No Drawings

COMPOSITIONS COMPRISING GLYCOSAMINOGLYCANS OF LOW VISCOSITY AND USE OF SAID COMPOSITION IN THERAPY OF CHRONIC CYSTITIS

This application is a national stage entry under 35 U.S.C. §371 of International Application No. PCT/EP2007/055107, filed May 25, 2007, which claims priority to Italian Patent Application No. MI2006A001030, filed on May 26, 2006, both of which are incorporated herein by reference in their entirety.

FIELD OF THE INVENTION

The present invention concerns new compositions comprising macromolecules, in particular glycosaminoglycans, intended for use in interstitial cystitis therapy.

PRIOR ART

Interstitial cystitis (IC) is a chronic illness that strikes mainly the female sex, causing a change in the bladder walls such that a gradual loss of function of said organ results. The precise etiopathogenesis of the illness is still unknown and there are various postulated hypotheses. A first hypothesis is that a defect exists in the lining layers that make up the bladder mucosa. This mucosal layer is formed of so called GAGs (glycosaminoglycans), a layer of mucopolysaccharides with water repellent properties which line the internal wall of the bladder rendering it impermeable to urine. In pathological conditions, and for still partly unknown reasons, the walls become permeable due to a loss of GAGs hence allowing urine to penetrate into the bladder wall causing irritation and inflammation. This change can be apparent in different ways, from a slight thinning of the urothelium to actual ulcers (so called Hunners ulcers).

The symptoms appear to be those typical of a cystitis attack: frequency, urgency, incontinence, dysuria, burning and/or suprapubic pain, pelvic, perineal, vaginal and anorectal pain. Bacteria absence in the urine is frequent even though, as a result of acquired changes to the mucosa, cases are seen where germs superimpose onto the inflammation. This further complicates diagnosis and consequently confuses the case history.

The ailments can be present singly, or in more severe cases, simultaneously. Often associated with the functional discomfort (up to 60 micturitions over a day and night) is an intense pain unresponsive to common analgesic therapies which prevents the patient from being able to have a normal relationship and sex life.

The chronic and progressive development of this pathology justifies the need for a correct and prompt diagnosis, enabling the correct therapy to be initiated. Despite this considerations it has been calculated that with a patient affected by interstitial cystitis, about 5-7 years and an average of 4-5 specialists are required before the correct diagnosis is reached. As the causes of interstitial cystitis are unknown, the treatments are aimed solely at alleviating symptoms. The effectiveness of most treatments remains nevertheless low and symptoms often return after a brief period of improvement or momentary recovery.

Sodium hyaluronate, a molecule which is part of the GAG group, is currently used for therapeutic purposes in the form of a very dilute solution (about 0.08-0.5% by weight) applied through a catheter. As an example, there is a solution currently on the market (with 0.08% active principle by weight) comprising 40 mg of sodium hyaluronate (CYSTISTAT®) in suitable 50 ml dosage units which needs to be on maintained inside the bladder for as long as possible. Although the relatively low content of active principle is disadvantageous on the one hand for the purposes of therapy, this limitation derives on the other hand from the physico-chemical characteristics of hyaluronic acid whose aqueous solutions exhibit an overproportional increase in viscosity with concentration. Therefore, an indiscriminate increase in active principle concentration (despite its excellent solubility in water) is not feasible for the therapeutic purposes considered herein, because the consequent substantial viscosity increase would render application of the solution through a catheter difficult and increasingly painful. Consequently, in preparing therapeutic solutions it is not possible to make use of extended regions of the solubility range of hyaluronic acid; in order to intensify the known therapy, therefore, increasing the frequency of the full extent extended regions of applications of the dilute solutions remains the only option.

This is because hyaluronic acid, despite its relatively simple chemical structure, is known to exhibit very complex biophysical properties in aqueous solution, see for example T. Hardingham, "Solution Properties of Hyaluronan" (1), properties and mechanisms which have not yet been studied from the viewpoint of increasing therapeutic concentrations for interstitial cystitis treatment.

Further to hyaluronic acid, the use of chondroitin sulfate, also a GAG, has been considered as an alternative active principle, preferably as its sodium salt in a 0.2% by weight aqueous solution (URACYST®).

Despite the existence of therapeutic compositions which comprise a single GAG as active principle as aforesaid, combined solutions have not yet been established. Indeed, it is known that the association of hyaluronic acid with chondroitin sulfate would accentuate the problem of low active principle concentration in the therapeutic solutions, since this association actually produces a further overproportional viscosity increase due to the known characteristic of the two molecules to autoaggregate (Scott 2, 3). This characteristic is described and already used in the pharmaceutical field, albeit different from the one discussed in the present Application, for example in EP 136782 which teaches that the association of hyaluronic acid with chondroitin sulfate and/or their salts produces a viscosity increase in the solutions that is greater than the sum of the viscosities produced by the single components. In EP 136782, this effect is then used for the purpose of preparing compositions for protecting corneal surface tissue. Hence, from this it already appears that these two active principles combined in a single solution for use in interstitial cystitis therapy would reduce—given the further viscosity increase—rather than increase the active principle quantities able to be conveyed to the damaged mucosae.

Consequently, there is still no solution to the technical problem of providing new compositions, preferably for interstitial cystitis therapy, which allow higher quantities of active principle, biopolymers in particular and preferably glycosaminoglycan mixes, to be conveyed to the damaged mucosae. Preferably the new compositions should be administratable via a catheter, in particular within the sphere of bladder instillation.

SUMMARY OF THE INVENTION

The inventors of the present Application have now surprisingly found that the technical problem identified above is resolved by the provision of a new aqueous composition comprising hyaluronic acid, chondroitin sulfate or salts thereof and bivalent metal ions, characterized in that the solution viscosity is lower than that of the same solution but without said bivalent metal ions.

DETAILED DESCRIPTION OF THE INVENTION

As indicated above, the inventors of the present Application have now found that is possible to prepare aqueous compositions which comprise hyaluronic acid, chondroitin sulfate or salts thereof and pharmaceutically acceptable bivalent metals ions, in particular calcium or magnesium, and which exhibit a controlled viscosity that is lower than the solution without bivalent metals ions. For the first time, this makes it possible to increase the quantities of active principle, in particular glycosaminoglycan combinations, contained in a composition for the therapy, for example, of interstitial cystitis, compared with the known art.

This is because the viscosity of the solutions of the present invention has been found to be lower than the viscosity of solutions comprising hyaluronic acid and chondroitin sulfate as acids, sodium salts or generally monovalent salts. This effect is particularly pronounced with the calcium ion.

This result is completely unexpected in that, as previously stated, not only has the autoaggregation effect between hyaluronic acid and chondroitin sulfate been known and well described for some time, but this effect is also considered to give rise to the known natural Theological effect of connective tissue.

EP 136782, which concerns instead actual solutions for therapeutic use, teaches that the effect of overproportionality of viscosity obtained when using solutions containing both hyaluronic acid and chondroitin sulfate is not limited to the more commonly used sodium salts, but also extends to the use of the respective potassium, magnesium and calcium salts.

Therefore, the solution to the aforesaid technical problem, identified by the inventors of the present Application, whereby the presence of bivalent metal ions, and in particular the calcium ion, in an aqueous solution of hyaluronic acid and chondroitin sulfate or their salts reduces its viscosity and hence allows the respective concentrations to be increased, was unexpected. Alternatively, this characteristic enables a solution for the purposes of interstitial cystitis therapy to be obtained which is easier to handle for the same concentration of the individual components.

Likewise unforeseeable were the particularly beneficial results attained by the described present invention towards the pathology, as emerging from the clinical data presented herein.

Preferably, the aforesaid bivalent metal ions are pharmaceutically acceptable and are chosen from the group consisting of Ca and Mg, Ca being particularly preferred.

Preferably, in the compositions of the invention there is present a quantity from 0.05 to 10.0, preferably from 0.1 to 3.5 equivalents of bivalent metal ions, relative to the sum of the hyaluronic acid and chondroitin sulfate used. Even more preferably, there is present a quantity from 0.5 to 2.0 equivalents of bivalent metal ions, relative to the sum of the hyaluronic acid and chondroitin sulfate used. Particularly preferred is a composition in accordance with the invention in which 1 equivalent of bivalent metal ions is present, relative to the sum of the hyaluronic acid and chondroitin sulfate used.

Regarding the concentrations of active principles, compositions are preferred as above in which the hyaluronic acid or its salt is present at a concentration from 0.1% to 3% w/v, preferably from 0.8% to 2.0% w/v, and the chondroitin sulfate or its salt is present from 0.05% to 3% w/v, preferably from 0.1% to 2.5% w/v. Particularly preferred are compositions in which the hyaluronic acid and chondroitin sulfate or their salts are present at 1.6% and 2.0%, respectively, by weight/volume.

As appears from the following examples, the advantages gained by the present invention are also maintained in the case of subsequent treatments, such as autoclave sterilization.

EXPERIMENTAL PART a. Exploring the Effect of Adding a Bivalent Ion to Various Concentrations of Sodium Hyaluronate, Chondroitin Sodium Sulfate and Combinations Thereof In examples 1-22 to follow and shown in table 1 below, the effect was explored of introducing a bivalent ion (calcium, magnesium) into preparations comprising sodium hyaluronate (molecular weight $1.5 \times 10^6$ Da) at concentrations of 0.8% and 1.6% by weight, and/or chondroitin sodium sulfate at concentrations of 0.2% and 2.0% by weight. Additions of $CaCl_2$ and $MgSO_4$ as shown in table 1 below were always undertaken in equimolar amounts relative to the active principles used. The dynamic viscosity values [mPa*s] obtained were measured with a rotational viscometer (Contraves, Rheomat 115) at the stated temperatures, and represent the mean apparent viscosities of the fluid under study.

In particular, for examples 1-2, 400 mg and 800.1 mg of sodium hyaluronate, mw $1.5 \times 10^6$ Da, were dissolved in purified water to a final volume of 50.0 ml. The solution was filtered through a 0.8 µm hydrophilic filter and viscosity was measured.

For examples 3-4, 100.0 mg and 1000.2 mg, respectively, of chondroitin sodium sulfate were dissolved in purified water to a final volume of 50.0 ml. The solution was filtered through a 0.8 µm hydrophilic filter and viscosity was measured.

For examples 5-8 the following solutions were prepared:
Solution A:
10.0 g of $CaCl_2$ dissolved in purified water in a 100.0 ml flask.

Example 5

400.2 mg of sodium hyaluronate, mw $1.5 \times 10^6$ Da, were dissolved in about 40 ml of purified water. 0.553 ml of solution A were added to the clear solution thus obtained, then purified water to bring the final volume to 50.0 ml. The solution was filtered through a 0.8 µm hydrophilic filter and viscosity was measured.

Example 6

800.2 mg of sodium hyaluronate, mw $1.5 \times 10^6$ Da, were dissolved in about 40 ml of purified water. 1.106 ml of solution A were added to the clear solution thus obtained, then purified water to bring the final volume to 50.0 ml. The solution was filtered through a 0.8 µm hydrophilic filter and viscosity was measured.

Example 7

100.3 mg of chondroitin sodium sulfate were dissolved in about 40 ml of purified water. 0.221 ml of solution A were added to the clear solution thus obtained, then purified water to bring the final volume to 50.0 ml. The solution was filtered through a 0.8 µm hydrophilic filter and viscosity was measured.

Example 8

1000.0 mg of chondroitin sodium sulfate were dissolved in about 40 ml of purified water. 2.205 ml of solution A were added to the clear solution thus obtained, then purified water to bring the final volume to 50.0 ml. The solution was filtered through a 0.8 µm hydrophilic filter and viscosity was measured.

For examples 9-11 the following solutions were prepared:

Example 9

400.0 mg of sodium hyaluronate, mw $1.5 \times 10^6$ Da, were dissolved in about 40 ml of purified water. 1000.1 ml of chondroitin-sodium sulfate were added to the clear solution thus obtained, then purified water to bring the final volume to 50.0 ml. The solution was filtered through a 0.8 µm hydrophilic filter and viscosity was measured.

Example 10

800.0 mg of sodium hyaluronate, mw $1.5 \times 10^6$ Da, were dissolved in about 40 ml of purified water. 100.1 ml of chondroitin sodium sulfate were added to the clear solution thus obtained, then purified water to bring the final volume to 50.0 ml. The solution was filtered through a 0.8 µm hydrophilic filter and viscosity was measured.

Example 11

800.1 mg of sodium hyaluronate, mw $1.5 \times 10^6$ Da, were dissolved in about 40 ml of purified water. 1000.1 ml of chondroitin sodium sulfate were added to the clear solution thus obtained, then purified water to bring the final volume to 50.0 ml. The solution was filtered through a 0.8 µm hydrophilic filter and viscosity was measured.

For examples 12-14 the following solutions were prepared:

Example 12

400.0 mg of sodium hyaluronate, mw $1.5 \times 10^6$ Da, were dissolved in about 35 ml of purified water. 2.758 ml of solution A were added to the clear solution thus obtained. The solution was subjected to magnetic agitation for about 1 minute and subsequently 1000.0 mg of chondroitin sodium sulfate were added. The clear solution thus obtained was brought to a final volume of 50 ml. The solution was filtered through a 0.8 µm hydrophilic filter and viscosity was measured.

Example 13

800.2 mg of sodium hyaluronate, mw $1.5 \times 10^6$ Da, were dissolved in about 35 ml of purified water. 1.327 ml of solution A were added to the clear solution thus obtained. The solution was subjected to magnetic agitation for about 1 minute and subsequently 100.3 mg of chondroitin sodium sulfate were added. The clear solution thus obtained was brought to a final volume of 50 ml. The solution was filtered through a 0.8 µm hydrophilic filter and viscosity was measured.

Example 14

800.3 mg of sodium hyaluronate, mw $1.5 \times 10^6$ Da, were dissolved in about 35 ml of purified water. 3.311 ml of solution A were added to the clear solution thus obtained. The solution was subjected to magnetic agitation for about 1 minute and subsequently 1000.1 mg of chondroitin sodium sulfate were added. The clear solution thus obtained was brought to a final volume of 50 ml. The solution was filtered through a 0.8 µm hydrophilic filter and viscosity was measured.

For examples 15-17 the following solutions were prepared:

Example 15

1000.2 mg of chondroitin sulfate were dissolved in about 35 ml of purified water. 2.758 ml of solution A were added to the clear solution thus obtained. The solution was subjected to magnetic agitation for about 1 minute and subsequently 400.2 mg of sodium hyaluronate, mw $1.5 \times 10^6$ Da, were added. Purified water was added to the clear solution to bring the final volume to 50 ml. The solution was filtered through a 0.8 µm hydrophilic filter and viscosity was measured.

Example 16

100.3 mg of chondroitin sulfate were dissolved in about 35 ml of purified water. 1.327 ml of solution A were added to the clear solution thus obtained. The solution was subjected to magnetic agitation for about 1 minute and subsequently 800.2 mg of sodium hyaluronate, mw $1.5 \times 10^6$ Da, were added. Purified water was added to the clear solution to bring the final volume to 50 ml. The solution was filtered through a 0.8 µm hydrophilic filter and viscosity was measured.

Example 17

1000.1 mg of chondroitin sulfate were dissolved in about 35 ml of purified water. 3.311 ml of solution A were added to the clear solution thus obtained. The solution was subjected to magnetic agitation for about 1 minute and subsequently 800.2 mg of sodium hyaluronate, mw $1.5 \times 10^6$ Da, were added. Purified water was added to the clear solution to bring the final volume to 50 ml. The solution was filtered through a 0.8 µm hydrophilic filter and viscosity was measured.

For examples 18-20 the following solutions were prepared:

Example 18

400.1 mg of sodium hyaluronate, mw $1.5 \times 10^6$ Da, were dissolved in about 35 ml of purified water. 1000.1 mg of chondroitin sodium sulfate were added to the clear solution thus obtained. 2.758 ml of solution A were added to the clear solution thus obtained. The solution was maintained under magnetic agitation for about 1 minute then brought to a final volume of 50 ml with purified water. The solution was filtered through a 0.8 µm hydrophilic filter and viscosity was measured.

Example 19

800.2 mg of sodium hyaluronate, mw $1.5 \times 10^6$ Da, were dissolved in about 35 ml of purified water. 100.1 mg of chondroitin sodium sulfate were added to the clear solution thus obtained. 1.327 ml of solution A were added to the clear solution thus obtained. The solution was maintained under magnetic agitation for about 1 minute then brought to a final volume of 50 ml with purified water. The solution was filtered through a 0.8 µm hydrophilic filter and viscosity was measured.

Example 20

800.1 mg of sodium hyaluronate, mw $1.5 \times 10^6$ Da, were dissolved in about 35 ml of purified water. 1000.1 mg of chondroitin sodium sulfate were added to the clear solution thus obtained. 3.311 ml of solution A were added to the clear solution thus obtained. The solution was maintained under magnetic agitation for about 1 minute then brought to a final volume of 50 ml with purified water.

The solution was filtered through a 0.8 μm hydrophilic filter and viscosity was measured.

For examples 21-22 the following solutions were prepared:
Solution B 10.00 g of $MgSO_4$ dissolved in purified water in a 100.0 ml flask.

Example 21

400.2 mg of sodium hyaluronate, mw $1.5 \times 10^6$ Da, were dissolved in about 35 ml of purified water. 1000.0 mg of chondroitin sodium sulfate were added to the clear solution thus obtained. 2.993 ml of solution B were added to the clear solution thus obtained. The solution was maintained under magnetic agitation for about 1 minute then brought to a final volume of 50 ml with purified water. The solution was filtered through a 0.8 μm hydrophilic filter and viscosity was measured.

Example 22

800.2 mg of sodium hyaluronate, mw $1.5 \times 10^6$ Da, were dissolved in about 35 ml of purified water. 100.0 mg of chondroitin sodium sulfate were added to the clear solution thus obtained. 1.440 ml of solution B were added to the clear solution thus obtained. The solution was maintained under magnetic agitation for about 1 minute then brought to a final volume of 50 ml with purified water. The solution was filtered through a 0.8 μm hydrophilic filter and viscosity was measured.

TABLE 1

| Solution No. | Solution | Viscosity at 25° C. (mPa * s) | Viscosity at 37° C. (mPa * s) |
|---|---|---|---|
| 1 | HA 0.8% | 548.51 | 428.25 |
| 2 | HA 1.6% | 2578.50 | 2191.15 |
| 3 | CHS Na 0.2% | 1.24 | 0.90 |
| 4 | CHS Na 2.0% | 2.47 | 2.03 |
| 5 | HA 0.8% + $CaCl_2$ | 351.45 | 247.60 |
| 6 | HA 1.6% + $CaCl_2$ | 1953.74 | 1512.24 |
| 7 | CHS Na 0.2% + $CaCl_2$ | 1.12 | 0.79 |
| 8 | CHS Na 2.0% + $CaCl_2$ | 2.07 | 1.73 |
| 9 | HA 0.8% + CHS Na 2.0% | 646.67 | 508.79 |
| 10 | HA 1.6% + CHS Na 0.2% | 3265.17 | 2824.02 |
| 11 | HA 1.6% + CHS Na 2.0% | 3105.10 | 2430.32 |
| 12 | HA 0.8% + $CaCl_2$ + CHS Na 2.0% | 360.34 | 268.60 |
| 13 | HA 1.6% + $CaCl_2$ + CHS Na 0.2% | 2561.74 | 2187.55 |
| 14 | Ha 1.6% + $CaCl_2$ + CHS Na 2.0% | 2105.75 | 1840.88 |
| 15 | CHS Na 2.0% + $CaCl_2$ + HA 0.8% | 364.58 | 264.78 |
| 16 | CHS Na 0.2% + $CaCl_2$ + HA 1.6% | 2705.99 | 2453.19 |
| 17 | CHS Na 2.0% + $CaCl_2$ + HA 1.6% | 2502.71 | 2048.27 |
| 18 | HA 0.8% + CHS Na 2.0% + $CaCl_2$ | 346.15 | 230.97 |
| 19 | HA 1.6% + CHS Na 0.2% + $CaCl_2$ | 2391.05 | 1876.94 |
| 20 | HA 1.6% + CHS Na 2.0% + $CaCl_2$ | 2401.61 | 1874.85 |
| 21 | HA 0.8% + CHS Na 2.0% + $MgSO_4$ | 382.81 | 301.10 |
| 22 | HA 1.6% + CHS Na 0.2% + $MgSO_4$ | 2719.15 | 2232.83 |

From the above data it is deduced that introducing the calcium ion, and also the magnesium ion, causes a decrease in viscosity of the solutions comprising sodium hyaluronate and chondroitin sodium sulfate. It is also deduced that said effect does not greatly depend on the preparation sequence of said solutions. Furthermore, it is also deduced that said viscosity decrease is apparent even at a temperature higher than ambient temperature, for example at body temperature. It therefore appears that the viscosities of solutions comprising hyaluronate and chondroitin sulfate (being higher than those of the individual solutions) can be reduced by co-formulation with bivalent metal ions. Therefore, by adding bivalent metal ions it will be possible to obtain more concentrated solutions that nevertheless exhibit the same viscosity as more dilute solutions comprising the two active principles, but without bivalent metal ions.

B. Exploring the Effect of Adding a Bivalent Ion, in the Presence of Chondroitin Sulfate, to Sodium Hyaluronate of Various Molecular Weights In examples 23-28 to follow and shown in table 2 below, the effect was explored of introducing a bivalent ion (calcium) into preparations comprising sodium hyaluronate (molecular weights of $9.33 \times 10^4$ Da, $3 \times 10^5$ Da and $1.5 \times 10^6$ Da, respectively) at concentrations of 1.6% by weight, and chondroitin sodium sulfate at concentrations of 2.0% by weight. Additions of $CaCl_2$ as shown below were always undertaken in equimolar amounts relative to the active principles used. The dynamic viscosity values [mPa*s] obtained were measured with a rotational viscometer (Contrakes, Rheomat 115) at the stated temperatures, and represent the mean apparent viscosities of the fluid under study.

In particular, for examples 23, 25, and 27 the following solutions were prepared:

Example 23

800.0 mg of sodium hyaluronate, mw $9.33 \times 10^4$ Da, were dissolved in about 35 ml of purified water. 1000.0 mg of chondroitin sulfate were added to the clear solution thus obtained. Purified water was added to the clear solution to bring the final volume to 50.0 ml. The solution was filtered through a 0.8 μm hydrophilic filter and viscosity was measured.

Example 25

800.0 mg of sodium hyaluronate, mw $3.0 \times 10^5$ Da, were dissolved in about 35 ml of purified water. 1000.0 mg of chondroitin sodium sulfate were added to the clear solution thus obtained. The solution was brought to a final volume of 50 ml with purified water. The solution was filtered through a 0.8 μm hydrophilic filter and viscosity was measured.

Example 27

800.0 mg of sodium hyaluronate, mw $1.5 \times 10^5$ Da, were dissolved in about 35 ml of purified water. 1000.0 mg of chondroitin sodium sulfate were added to the clear solution thus obtained. The solution was brought to a final volume of 50 ml with purified water. The solution was filtered through a 0.8 μm hydrophilic filter and viscosity was measured.

In particular, for examples 24, 26, and 28 the following solutions were prepared:

Example 24

800.1 mg of sodium hyaluronate, mw $9.33 \times 10^4$ Da, were dissolved in about 35 ml of purified water. 1000.1 mg of chondroitin sodium sulfate and 3.311 ml of solution A were added to the clear solution thus obtained. The clear solution thus obtained was brought to a final volume of 50 ml with purified water. The solution was filtered through a 0.8 μm hydrophilic filter and viscosity was measured.

Example 26

800.1 mg of sodium hyaluronate, mw 3.0×10⁵ Da, were dissolved in about 35 ml of purified water. 1000.0 mg of chondroitin sodium sulfate and 3.311 ml of solution A were added to the clear solution thus obtained. The clear solution thus obtained was brought to a final volume of 50 ml with purified water. The solution was filtered through a 0.8 μm hydrophilic filter and viscosity was measured.

Example 28

800.1 mg of sodium hyaluronate, mw 1.5×10⁶ Da, were dissolved in about 35 ml of purified water. 1000.0 mg of chondroitin sodium sulfate and 3.311 ml of solution A were added to the clear solution thus obtained. The clear solution thus obtained was brought to a final volume of 50 ml with purified water. The solution was filtered through a 0.8 μm hydrophilic filter and viscosity was measured.

The viscosity of solutions 23-28 above was measured as such and after autoclave sterilization (121° C. for 15 minutes).

TABLE 2

Variation in viscosity vs MW and sterilization

| Solution | | Viscosity (mPa * s) T25° C. | Viscosity after sterilization (mPa * s) T25° C. |
|---|---|---|---|
| 23 | HA 1.6% (MW ca. 100000 + CHS Na 2.0% | 26.848 | 11.845 |
| 24 | HA 1.6% (MW ca. 100000) + $CaCl_2$ + CHS Na 2.0% | 20.840 | 8.629 |
| 25 | HA 1.6% (MW 300000) + CHS Na 2.0% | 201.210 | 47.126 |
| 26 | HA 1.6% (MW 300000) + $CaCl_2$ + CHS Na 2.0% | 164.520 | 26.720 |
| 27 | HA 1.6% (MW 1500000) + CHS Na 2.0% | 3164.610 | 191.170 |
| 28 | HA 1.6% (MW 1500000) + $CaCl_2$ + CHS Na 2.0% | 2291.350 | 61.040 |

From the above results it is deduced that the ability of bivalent metal ions, in particular the calcium ion, to reduce the viscosity of aqueous solutions comprising hyaluronate and chondroitin sulfate is apparent for hyaluronates of different molecular weights. Moreover, it appears that said effect is maintained even under severe conditions, such as autoclave sterilization. Therefore, co-formulation of bivalent metal ions with hyaluronate and chondroitin sulfate with the aim of reducing the resulting viscosity is also indicated for solutions subjected to this type of treatment.

C. Clinical Tests

The solution as prepared in example 29 to follow was measured with the same viscometer used for preceding examples 1-28.

Example 29

A solution of 1.6% (w/v) high molecular weight sodium hyaluronate (1.8×10⁶ Da), 2.0% (w/v) chondroitin sodium sulfate and $CaCl_2$ in a quantity equivalent to the total sodium.

Solution A

Dissolve 132.52 g of anhydrous $CaCl_2$ in 2000 g of distilled water under magnetic agitation.

Solution B

Dissolve 319.7 g of sodium hyaluronate in 17246 g of distilled water under magnetic agitation. Add 422.0 g of chondroitin sodium sulfate and solution A to the clear and transparent solution under magnetic agitation. Leave under agitation for about 1 hour. Filter the solution through a 1.2 μm filter.

Solution density: 1.006 g/ml.

Solution viscosity: 2364.07 mPa*s.

The solution is sterilized in an autoclave (121° C. for 15 minutes).

Solution viscosity after sterilization: 49.44 mPa*s.

The sterilized solution was then used in the tests below.

Example 30

10 patients affected by interstitial cystitis for at least 2 years were subjected to treatment with the product derived from example 29. Administration was by bladder instillation.

The inclusion criteria for interstitial cystitis diagnosis had to comply with those established by the European Study Society on Interstitial Cystitis (ESSIC).

All the patients had already undergone drug treatment currently available for this pathology, with unsatisfactory results.

Patient data were handled in compliance with current privacy laws.

The aim of the study is to confirm the results of said therapy by assessing its effects on bladder function by way of a voiding diary and morphofunctional tests, and assessing the impact on quality of life through the use of: O'Leary Sant, PUF, Sexuality and Wexner questionnaires.

Treatment duration was four months, the minimum time useful for assessing the preliminary results, and sufficient to encourage, or otherwise, continuation of the therapy. In particular, we assessed the effects on the more significant symptoms of this pathology (pain, urination frequency and urgency), besides any improvements or otherwise that said therapy has on quality of life.

Assessment of the O'Leary Sant questionnaire on QoL, undertaken on a monthly basis, enabled a positive improvement trend to be clearly shown, both by assessing the questionnaire as a whole and specifically the two domains: symptoms and problems.

The Pain Urgency Frequency (PUF) questionnaire enabled an improvement to be clearly shown for three main symptoms, both as a whole and in the two domains: symptoms and bothers. In the following tables the subjective results in accordance with O'Leary Sant (Table 3) and Pain Urgency Frequency (PUF) (Table 4) are given, together with objectives such as number of micturitions, mean micturition volume and mean bladder capacity (table 5). The last two lines give the means and percentage differences.

TABLE 3

Subjective assessment according to O'Leary Sant

| Id. | Age | Height | Weight | Ps | Po | Tc | Menopause | O'Leary Pre | O'Leary 12 Weeks |
|---|---|---|---|---|---|---|---|---|---|
| 1 | 64 | 163 | 86 | 0 | 0 | 2 | YES | 30 | 25 |
| 2 | 34 | 169 | 55 | 0 | 0 | 0 | NO | 20 | 18 |
| 3 | 59 | 163 | 63 | 0 | 0 | 2 | YES | 23 | 17 |
| 4 | 49 | 162 | 68 | 2 | 0 | 0 | YES | 24 | 23 |
| 5 | 51 | 158 | 48 | 1 | 0 | 0 | YES | 26 | 25 |
| 6 | 65 | 157 | 55 | 2 | 0 | 0 | YES | 36 | 26 |
| 7 | 49 | 155 | 62 | 0 | 0 | 1 | YES | 22 | 10 |
| 8 | 44 | 161 | 70 | 2 | 0 | 0 | NO | 26 | 22 |
| 9 | 46 | 152 | 58 | 1 | 0 | 0 | YES | 26 | 20 |
| 10 | 63 | 160 | 62 | 2 | 0 | 0 | YES | 37 | 23 |
| | | | | | | | mean | 27 | 21 |
| | | | | | | | % variation | 100 | 23% |

TABLE 4

Subjective assessment according to Pain Urgency Frequency

| Id. | Age | Height | Weight | Ps | Po | Tc | Menopause | PUF Pre | PUF 12 Weeks |
|---|---|---|---|---|---|---|---|---|---|
| 1 | 64 | 163 | 86 | 0 | 0 | 2 | YES | 31 | 18 |
| 2 | 34 | 169 | 55 | 0 | 0 | 0 | NO | 20 | 13 |
| 3 | 59 | 163 | 63 | 0 | 0 | 2 | YES | 16 | 6 |
| 4 | 49 | 162 | 68 | 2 | 0 | 0 | YES | 26 | 17 |
| 5 | 51 | 158 | 48 | 1 | 0 | 0 | YES | 24 | 17 |
| 6 | 65 | 157 | 55 | 2 | 0 | 0 | YES | 23 | 20 |
| 7 | 49 | 155 | 62 | 0 | 0 | 1 | YES | 21 | 12 |
| 8 | 44 | 161 | 70 | 2 | 0 | 0 | NO | 22 | 24 |
| 9 | 46 | 152 | 58 | 1 | 0 | 0 | YES | 25 | 26 |
| 10 | 63 | 160 | 62 | 2 | 0 | 0 | YES | 23 | 15 |
| | | | | | | | mean | 23 | 17 |
| | | | | | | | % variation | 100 | 27% |

TABLE 5

Objective assessment. Number and volume of micturitions and bladder capacity

| No. Micturitions Pre | Mean Micturition Pre | Mean Capacity Pre | No. Micturitions 12 weeks | Mean Micturition (12 weeks) | Mean capacity (12 weeks) |
|---|---|---|---|---|---|
| 39 | 1400 | 43 | 33 | 1917 | 58 |
| 22 | 1091 | 50 | 25 | 988 | 40 |
| 10 | 1772 | 184 | 7 | 1343 | 192 |
| 10 | 933 | 97 | 7 | 1893 | 270 |
| 18 | 3300 | 165 | 16 | 2490 | 158 |
| 15 | 2360 | 157 | 16 | 2312 | 144 |
| 16 | 3960 | 238 | 10 | 2183 | 227 |
| 13 | 2400 | 189 | 8 | 1593 | 199 |
| 31 | 3110 | 103 | 27 | 2792 | 100 |
| 9 | 1277 | 137 | 9 | 1400 | 160 |
| 18 | 2160 | 136 | 16 | 1891 | 155 |
| 100 | 100 | 100 | 14% | 12% | 12% |

Subjective assessments following 12 weeks of treatment show a 23-27% improvement, with a 14% decline in the number of micturitions, a 12% reduction in mean micturition and a 12% increase in bladder capacity.

REFERENCES

1. Tim Hardingham, Solution Properties of Hyaluronan—From Chemistry and Biology of Hyaluronan—Hari G. Garg and Charles A. Hales Editors-Elsevier (Amsterdam).
2. Scott E. J., Heatley F., Hyaluronan forms specific stable tertiary structures in aqueous solution: A $^{13}C$ NMR study—Proc. Natl. Acad. Sci. USA vol 96 4850-4855 (1999).
3. Scott E. J. Structure and function in extracellular matrices depend on interaction between anionic glycosaminoglycans—Pathol. Biol. 49, 284-289 (2001).

The invention claimed is:

1. An aqueous pharmaceutical composition for bladder instillation, cystitis therapy, or interstitial cystitis therapy, the aqueous composition comprising water, hyaluronic acid or a salt thereof and/or chondroitin sulphate or a salt thereof, and a pharmaceutically acceptable bivalent metal ion, wherein the bivalent metal ion is chosen from calcium and magnesium, and wherein the bivalent metal ion is present in an amount effective to lower the viscosity of the composition.

2. Composition as claimed in claim 1 wherein the bivalent metal is a calcium ion.

3. Composition as claimed in claim 1 wherein from 0.05 to 10.0 equivalents of bivalent metal ions are present relative to the sum of the hyaluronic acid and chondroitin sulfate present.

4. Composition as claimed in claim 3 wherein from 0.5 to 2.0 equivalents of bivalent metal ions are present relative to the sum of the hyaluronic acid and chondroitin sulfate present.

5. Composition as claimed in claim 1 wherein the hyaluronic acid or a salt thereof is present in a concentration from 0.1% to 3% w/v and the chondroitin sulfate or a salt thereof is present in a concentration from 0.05% to 3% w/v.

6. Composition as claimed in claim 5 wherein the hyaluronic acid and the chondroitin sulfate or their salts are present at 1.6% and 2.0%, respectively, by weight/volume.

7. Composition as claimed in claim 1, sterilized in an autoclave.

8. Composition as claimed in claim 3 wherein from 0.1 to 3.5 equivalents of bivalent metal ions are present relative to the sum of the hyaluronic acid and chondroitin sulfate present.

9. Composition as claimed in claim 4 wherein 1 equivalent of bivalent metal ions is present relative to the sum of the hyaluronic acid and chondroitin sulfate present.

10. Composition as claimed in claim 5 wherein the hyaluronic acid or a salt thereof is present in a concentration from 0.8% to 2.0% w/v, and the chondroitin sulfate or a salt thereof is present in a concentration from 0.1% to 2.5% w/v.

* * * * *